US 7,785,245 B2

(12) United States Patent
Markoll

(10) Patent No.: US 7,785,245 B2
(45) Date of Patent: Aug. 31, 2010

(54) PORTABLE APPLICATOR FOR PULSED SIGNAL THERAPY

(76) Inventor: Richard Markoll, Denninger Strasse 104, D-81925 München (DE)

( * ) Notice: Subject to any disclaimer, the term of this patent is extended or adjusted under 35 U.S.C. 154(b) by 1835 days.

(21) Appl. No.: 10/478,836

(22) PCT Filed: May 31, 2002

(86) PCT No.: PCT/EP02/06004

§ 371 (c)(1),
(2), (4) Date: Apr. 22, 2004

(87) PCT Pub. No.: WO02/096515

PCT Pub. Date: Dec. 5, 2002

(65) Prior Publication Data

US 2004/0176806 A1 Sep. 9, 2004

(30) Foreign Application Priority Data

May 31, 2001 (DE) .................. 101 26 607

(51) Int. Cl.
*A61N 1/00* (2006.01)
(52) U.S. Cl. ...................................... 600/14
(58) Field of Classification Search ............ 600/9–15; 606/32, 33, 34, 41, 42, 53; 607/1, 2, 3, 65–76, 607/103, 115, 139, 144–150; 128/897, 898
See application file for complete search history.

(56) References Cited

U.S. PATENT DOCUMENTS

| 2,831,193 | A | * | 4/1958 | Terry ........................... 2/46 |
| 5,000,178 | A | * | 3/1991 | Griffith ....................... 607/2 |
| 5,067,940 | A | * | 11/1991 | Liboff et al. ................ 600/13 |
| 5,181,902 | A | * | 1/1993 | Erickson et al. ............ 600/13 |
| 5,224,922 | A | * | 7/1993 | Kurtz ........................ 600/13 |
| 5,269,747 | A | * | 12/1993 | Erickson et al. ............ 600/14 |
| 5,344,384 | A | * | 9/1994 | Ostrow et al. ............... 600/13 |
| 5,458,628 | A | * | 10/1995 | Cipolla ..................... 607/112 |
| 5,620,463 | A | * | 4/1997 | Drolet ........................ 607/3 |
| 5,984,854 | A | * | 11/1999 | Ishikawa et al. ............ 600/9 |
| 6,132,362 | A | * | 10/2000 | Tepper et al. .............. 600/14 |
| 6,186,941 | B1 | * | 2/2001 | Blackwell .................. 600/13 |

FOREIGN PATENT DOCUMENTS

| DE | 3828043 A1 | 5/1989 |
| DE | 38 28 043 A1 | 11/1989 |
| DE | 19708542 A1 | 9/1998 |
| DE | 197 08 542 A1 | 10/1998 |
| EP | 0827993 B1 | 11/1999 |
| WO | WO 00/78267 A2 * | 12/2000 |

* cited by examiner

*Primary Examiner*—Charles A Marmor, II
*Assistant Examiner*—Christine D Hopkins
(74) *Attorney, Agent, or Firm*—The Nath Law Group; Jerald L. Meyer; Sungyeop Chung

(57) ABSTRACT

A portable applicator (20) for pulsed signal therapy comprises: an elastic supporting body (25), which can expand in a planar manner; at least two signal generating units (11, 12), which are arranged in or on the elastic supporting body (25) whereby being symmetric with regard to an axis of symmetry of the supporting body (25), and; a device for supplying a control signal (17, 18) to the signal generating units (11, 12).

2 Claims, 3 Drawing Sheets

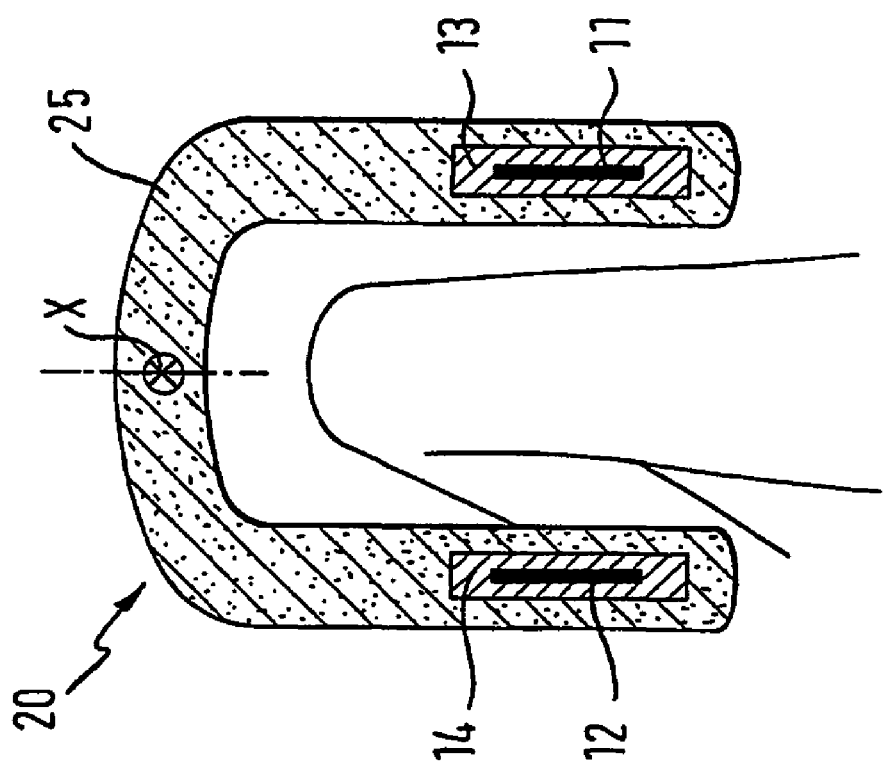

PORTABLE APPLICATOR FOR PULSED SIGNAL THERAPY

FIELD OF THE INVENTION

The invention relates to a portable applicator to be used for pulsed signal therapy to treat disorders of the musculoskeletal system or other physical conditions requiring treatment which respond to pulsed fields.

Hereby, it is essential that the pulsed fields are applied to the points of the body in a suitable strength and at a suitable frequency for a specific time in order to excite specific tissue systems in the body, for example the ions contained in the musculoskeletal system, for example in synovial fluids and soft tissue.

PRIOR ART

Known for this treatment are stationary devices comprising, for example, applicators with magnetic windings which generate magnetic fields of a predetermined strength and with a specific pulse frequency. These applicators are bulky and designed to permit treatment at a specific installation site, for example a doctor's practice. The patient's organs to be treated are placed in a suitable manner in these applicators, which are generally connected to frames, such as a bed, on which the patient may sit or lie.

A system of this kind is described, for example, in EP 0 528 964. This system comprises an annular coil which is used to generate a magnetic field in the interior of the coil. The magnetic field is directed at the body organ or tissue to be treated and has a field strength of less than 20 gauss. At the same time, the magnetic field is pulsed with a frequency of from 1 to 30 Hz (pulses/second).

The device described in this publication is in particular suitable for treating knee or elbow joints since the patient has to place the organ or body part in the field generated by the magnetic coil, i.e. has to guide the body organ through the coil. Since the coil is relatively unwieldy and rigid, the device is not suitable for transportation or mobile use.

A device suitable for mobile use is described in U.S. Pat. No. 5,269,747. Here, electromagnetic fields are generated by partially rigid signal transmitters of which there are two and which are anatomically shaped for a particular body organ. In the interior of these signal transmitters, there is a battery device which is also anatomically shaped. The two signal transmitters are connected on the one hand by a cable which transmits control signals from one signal transmitter to the other. In addition, there is an adjustable belt which forms an enclosed ring for attachment to the body. The signal transmitters are attached to this belt. The organ to be treated is, for example, the spine. The signal transmitters are, for example, constructed from two parallel primary windings with about seven windings each, a secondary winding with about 35 windings and a sensor winding with at least one winding. The signal generators are hereby at least partially in contact with the organ to be treated.

DESCRIPTION OF THE INVENTION

One object of the invention is to develop a portable applicator for pulsed signal therapy which is comfortable for the patient and at the same time may be effectively used for different organs and tissues. Another object of the invention is to develop a device for pulsed signal therapy which is portable and simple for a patient to operate.

This object is achieved by an applicator with the features of claim 1 and a device with the features of claim 15.

Hereby, the invention is based on the object of fixing signal generating units inside an elastic supporting body in such a way that, on the one hand, flexible use for different body organs is ensured; this is achieved by the symmetrical arrangement of the signal generating units in or on the supporting body.

In addition, the arrangement is preferably not enclosed, for example in a ring shape, but during the treatment lies in a U-shape around or on the patient's organ. The supporting body has a main plane in relation to which it can be spread over a surface. The symmetry plane, in relation to which the signal, generating units are arranged symmetrically, lies in this main plane and is preferably also a symmetry plane of the supporting body.

In addition, the object is also achieved by the fact that the signal generating units are secured in or on the elastic supporting body and that the supporting body can be spread over a surface. This means that the patient only comes into direct contact with the supporting body and not with the, for the most part, rigid and stiff signal generating units, which is pleasant for a patient due to the elasticity of the supporting body and does not cause any discomfort. The elasticity of the supporting body also prevents rigid parts or parts perceived as annoying for any other reason from coming into contact with the patient—instead the supporting body adapts to the anatomy of the body organ to be treated.

The symmetrical arrangement of the signal generating units enables the distance between the signal generating units to be varied when the applicator is placed on a body organ so that the applicator is equally suitable for different body organs, whereby within the body organ to be treated, the same pulsed signals may be generated for different body organs or the pulsed signals may be adapted to the organ in question, for example, with regard to their strength.

Advantageous embodiments are characterised by the other claims.

For example, according to one advantageous embodiment the signal generating units are embodied as annular coils. These annular coils may have an air core or a ferrite core. The use of annular coils as signal generating units facilitates the arrangement of these annular coils as a Helmholtz coil pair. For this, they are arranged and switched in series. This enables the elastic supporting body to be positioned appropriately around the joint to be treated whereby the signal generating units embedded therein or attached thereto are positioned in the form of annular coils in such a way that the preferably identical coils are arranged in parallel and coaxially to each other. In addition, if the annular coils are arranged in or on the supporting body in such a way that the distance between the annular coils is one to two ring coil radii, the annular coils as signal generating units may be placed around the organ to be treated in such a way that the distance between them is equal to one coil radius. This causes them to function as a Helmholtz pair and to generate an approximately uniform magnetic field in the space between the coils used to treat the body organ.

If a radius of from 2 to 20 cm, in particular approximately 3.5 to 4 cm, is chosen for the annular coils, this is suitable for the majority of body organs, in particular also for the most usual body sizes.

Advantageously, the supporting body has a kidney-shaped or bone-shaped form in cross section, i.e. in the section parallel to the main plane of the supporting body. This in turn facilitates the comfortable adaptation of the supporting body when it is placed around a body organ with the signal generating units. In particular when placed around a shoulder organ or similar, this will ensure the comfortable positioning of the applicator on the patient.

According to a preferred embodiment, at the least the external layer of the supporting body is formed of or coated with fabric material or neoprene. This ensures a pleasant sensation for the patient when the supporting body is placed around the patient's body organ to be treated. In addition, the fabric material and neoprene are relatively light materials so that the patient does not have to support any unnecessary applicator weight when the applicator is placed on the body organ to be treated during the relatively long treatment duration of up to and longer than one hour.

The signal generating units may preferably also be embedded in a protective body. This ensures that the signal generating units are accommodated robustly with protection against impact and/or damage inside the elastic supporting body or on it on a side facing away from the body organ during the treatment. Since the applicator is to be designed as a portable applicator which can be carried by the user with no problem and used in different locations, for example for treatment while the user is doing office work or sitting in front of the television, this is advantageous since the protective body protects the actual signal generating units from damage from impacts and the like.

A preferred protective body is, for example, a synthetic resin sheath, which may be soft, in which the signal generating units are embedded. A synthetic resin sheath of this kind may be designed as a compact body with smooth external surfaces so that no projections, sharp or pointed edges or similar on the signal generating units that could be annoying during the use of the applicator may be felt. In addition, it is simple and inexpensive to embed the signal generating units in synthetic resin sheaths of this kind used as protective bodies. A different type of protective body, for example a plastic casing or similar, is obviously also possible.

In accordance with a particularly preferred embodiment, the signal generating units, possibly embedded in a protective body, may be completely embedded in the elastic supporting body. This means that the user does not come into direct contact with the signal generating units or the protective bodies for the signal generating units which again may cause unpleasant sensations.

Preferably, the signal generating units generate a pulsed magnetic field with a field strength of less than 20 gauss between the signal generating units, i.e. in the area to be treated. Magnetic fields of this type have been found to be particularly effective for the treatment of diseases of the musculoskeletal system.

Advantageously, the signal generating units will be fed with a control signal in the form of pulsed DC voltage with a rate of from 1 to 30 pulses, more preferably from 1 to 12 pulses, per second, whereby the control signal has a quasi rectangular pulse shape with an abruptly rising and abruptly falling voltage. This enables fields which are particularly suitable for treating unusual conditions of the musculoskeletal system to be generated in the treatment area, i.e. the area between the signal generating units, when the applicator is placed on the body organ to be treated. These control signals are supplied by means of the device for feeding the control signals to the signal generating units.

Apart from the applicator according to any one of claims 1 to 14, the device for pulsed signal therapy comprises a control device with which it is easy for the user to switch the applicator on and off and, if appropriate, choose between different pulsed signal frequencies or different field strengths. In addition, according to a preferred embodiment, an external power supply unit may be provided that is connected to the control device and supplies the control device with the required electricity. According to preferred embodiments, the power supply unit may be detached from the control device and/or the control device may be detached from the applicator, which ensures that the device for pulsed signal therapy may be easily transported, for example, by accommodating the applicator, the control device and the power supply unit each in separate compartments of a transportation bag.

BRIEF DESCRIPTION OF THE DRAWING

The invention will now be further described, purely by way of example, with reference to the drawings in which FIG. 4 is a cross-sectional view through the applicator along the line y-y in FIG. 3 when the applicator is in treatment position.

WAYS TO CARRY OUT THE INVENTION

Figure 1:
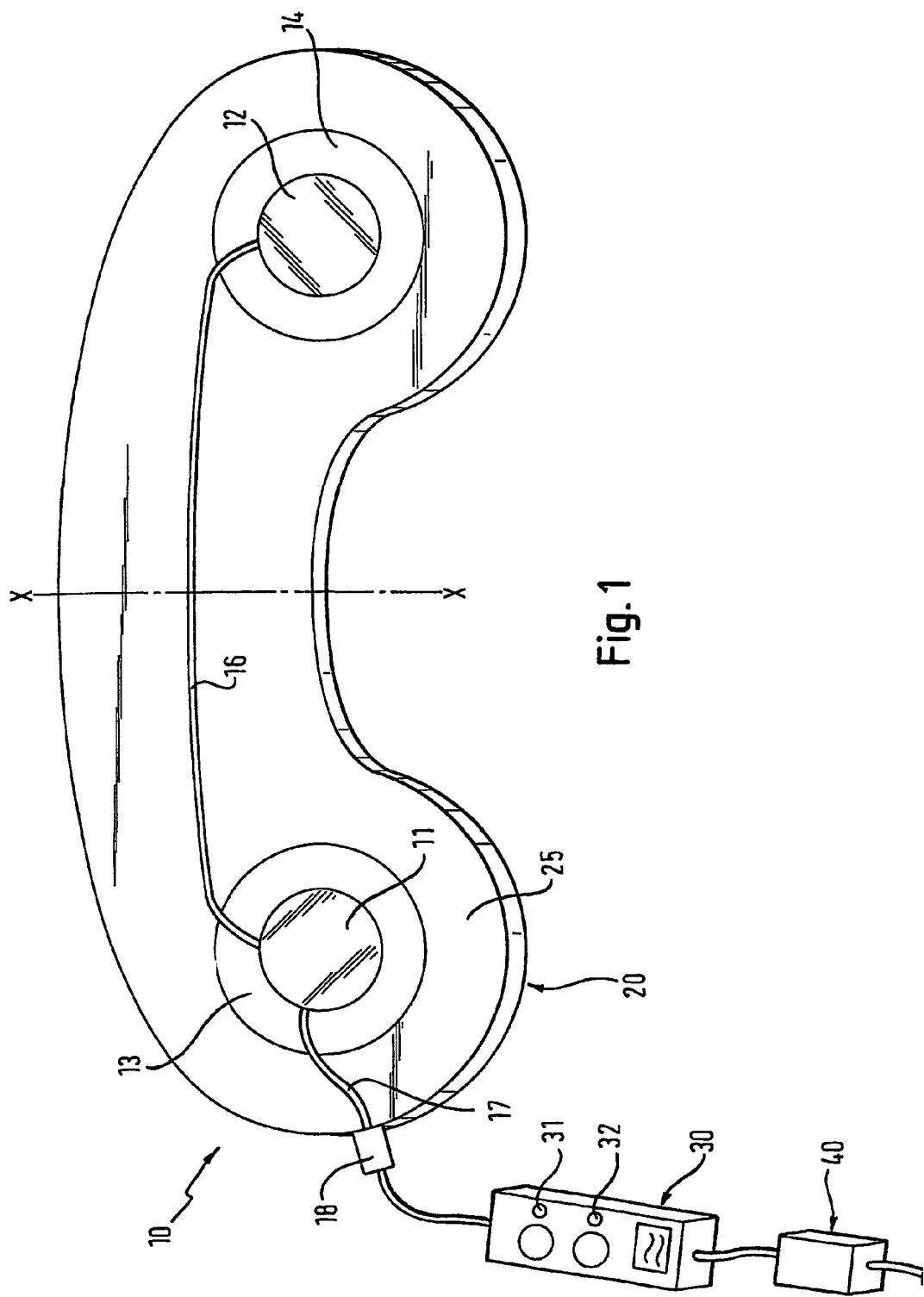
FIG. 1 is a schematic view of a device for pulsed signal therapy whereby the applicator is shown in partial cross section

FIG. 1 shows a device for pulsed signal therapy in a first embodiment. The device is generally indicated by the reference number 10. The device comprises an applicator 20, a control device 30 and a power supply unit 40 whereby the control device 30 is connected to the applicator 20 on the one hand and the power supply unit 40 on the other. The power supply unit 40 is used for connection to a normal mains network and may, if necessary, be adapted according to the different current strengths and voltages in different countries.

Provided on the control device 30 are various devices in order, on the one hand, to switch the applicator on and off and, on the other, to adjust the desired treatment strength and, if necessary, the treatment frequency depending on the type of signal generating units. Provided in this case are a device 31 for setting the field strength and a device 32 for setting a frequency with which the field is pulsed. The control device 30, the power supply unit 40 and the applicator 10 are connected detachably to each other, for example by a simple plug connection in the form of a conventional plug.

The power supply unit 40 and the control device 30 each have dimensions approximately in the range 10×15×10 cm so that they are each easy to transport. In the embodiment shown in FIG. 1, the applicator 20 is kidney-shaped. This shape is in particular favourable if the applicator might possibly also be used to treat the shoulder joint since the patient's neck will fit comfortably in the recess in the kidney shape.

Figure 3:
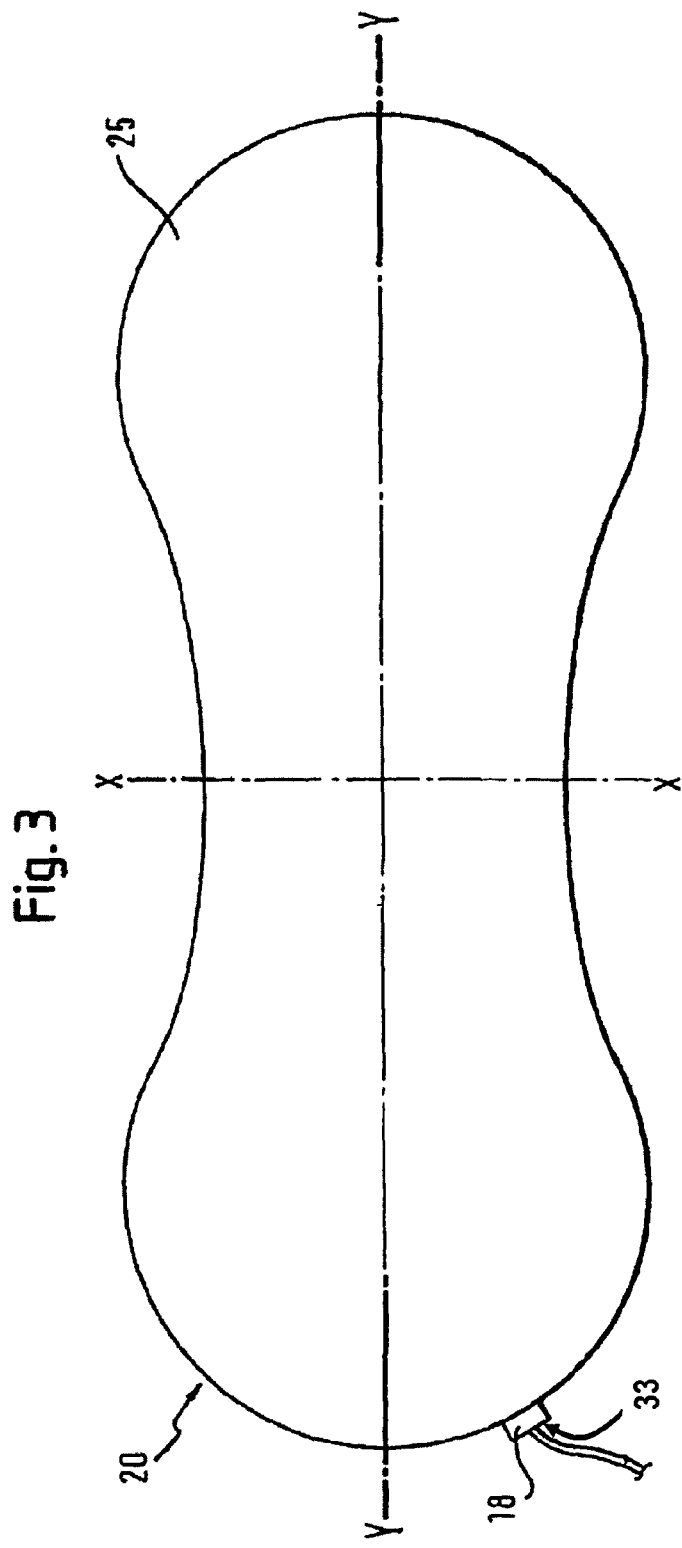
FIG. 3 is a second embodiment of the applicator.

In alternative embodiments, in the main plane, for example a top view, the applicator is bone-shaped, as shown in FIG. 3. Here the depth of the recess depends upon whether, for example, the shoulder joint is also to be treated with the applicator or only the knee or elbow joint or which other organs are to be treated. It is also possible for the recesses to be given different depths and radii on the two sides so that, depending upon the applicator's direction of rotation, it is always possible to find a comfortable position during use and so the patient does not experience any discomfort from the outline of the supporting body during treatment.

Obviously, it is also possible for the applicator to have an oval or rectangular shape, whereby these shapes are not preferred since the applicator is on the one hand less flexible in use and, on the other, will be more uncomfortable for the patient during the treatment of certain body organs.

In the embodiment shown in FIG. 1, there is a signal connection between the signal generating units 11, 12 shown schematically which are both embedded in protective bodies 13, 14. In the embodiment shown, the protective bodies 13, 14 take the form of relatively thick circular disks which is advantageous as they have few perceptible edges. However, their thickness is preferably restricted to the minimum degree possible required for the embedding of the signal generating units to ensure that the applicator is not unnecessarily bulky. Other alternative shapes for the protective bodies are, for example, lenticular shapes, which have even fewer perceptible edges, or even polygonal shapes or similar.

The signal generating units 11, 12 have a fixed position in the protective bodies 13, 14 so that their position relative to the protective bodies 13, 14 does not change during usage or transportation. In a similar way, the protective bodies 13, 14 are each positioned in the supporting body 25 in such a way that their position does not change either. This is possible, for example, due to the fact that the supporting body 25 is provided with notches or pockets corresponding to the shape of the protective bodies 13, 14 so that they are unable to move or only able move to an insignificant degree.

The supporting body 25 comprises one or more layers of an elastic material, for example neoprene or a fabric material, whereby the supporting body may also have a multi-layer structure. For example, it is also possible for one or more layers to be foam layers. Hereby, the supporting body should remain as soft as possible and to a certain extent elastic so that it may be placed around different body organs and be adapted to match the shape of body organs. In addition, it is advisable to provide cushioning in the area of the signal generating units and the signal generating units' protective bodies 13, 14—this may be provided, for example, by the neoprene layer—so that the user does not feel the protective bodies for the signal generating units and the signal generating units and possibly find them uncomfortable.

Figure 2:
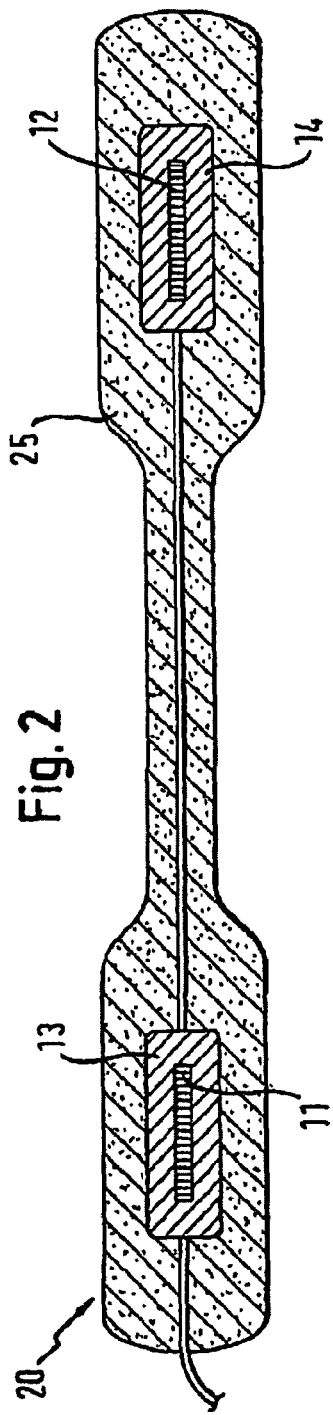
FIG. 2 is a cross-sectional view of the applicator

FIG. 2 shows as an example that in the area of the signal generating units 11, 12 and the protective bodies for the signal generating unit 13, 14, the supporting body's sheathing layer 25 is thickened so that the protective body forms a cushion for the protective bodies in this area and remains soft.

In any case, the supporting body 25 must be able to transmit the signals or pulsated fields generated in the signal generating units 11, 12.

Unlike the embodiment shown in FIG. 2, however, it is also possible to design the supporting body 25 with a uniform thickness in all areas. However, it is advantageous to have a taper in the area in which there are no signal generating units 11, 12 since this facilitates the elasticity and adaptability of the supporting body 25 to the body organ to be treated. It also saves weight.

The signal generating units 11, 12 may, for example, take the form of Helmholtz coils. Here, the annular coils 11, 12 may have an air or ferrite core.

The protective bodies 13, 14 are, for example, in the form of a synthetic resin sheath. It should be noted with regard to the dimensions that, in the case of Helmholtz coils, the annular coils 11, 12 have a radius of from 5 to 20 cm which has been found to be advantageous for the treatment of different body organs. The two coils 11, 12 are hereby identical and symmetrical relative to an axis of symmetry X-X of the supporting body (see FIG. 3). This enables the applicator 20 to be effectively positioned around a body organ (tissue or joint) so that the coils 11, 12 are aligned parallel to each other and coaxially, whereby advantageously the distance between the two coils and hence also the distance between each coil and the axis of symmetry X is dimensioned so that the distance between the two coils when they are aligned parallel to each other and coaxially and placed around a body organ corresponds approximately to the radius of one single coil. In this case, the coils function as a Helmholtz coil pair and generate an approximately uniform magnetic field in the space between the coils, with, depending upon the input signal applied by the control device 30, said field functioning as a pulsed field, whereby advantageously the field strength is less than 20 gauss and the pulse frequency is in the range of from 1 to 30 pulses/second.

For simple circuit control, the two signal generating units 11, 12, for example the coils as in the embodiment shown in FIGS. 1 and 2, have a suitable electrical connection 16 with each other. For connection to the control device, a connection cable 17 is provided on one of the coils 11 terminating in a plug connector 18. A suitably fitting plug connector 33 belonging to the control device 30 may be used in this plug connector.

In addition, care should be taken with regard to the applicator 20 that a light material as far as its weight is concerned is selected for the supporting body 25 so that the patient does not bear any unnecessary weight.

FIG. 4 is a schematic diagram showing how the applicator 20 is positioned around a body joint, here using the example of a knee. This clearly shows that during the treatment the signal generating units 11, 12 are essentially aligned parallel to each other whereby the applicator's 20 line of symmetry X-x is now perpendicular to the drawing plane.

The elasticity and the corresponding shape of the supporting body 25 for the applicator 20 enables the applicator to be suitably placed around different body organs. This permits the comfortable treatment of different body organs with the same applicator. In addition, due to its good elasticity, the applicator is easy to fold and hence easy to transport, in particular when the associated control device and, if applicable, power supply unit are detachable from the applicator 20.

The essential aspect of the invention is the fact that it develops an effective applicator for pulsed signal therapy which is suitable for mobile use.

The invention claimed is:

1. A device for pulsed signal therapy, comprising:
 a portable applicator for pulsed signal therapy comprising:
  an elastic supporting body which can be spread over a surface and during treatment lies in a U-shape around or on a body part to be treated;
  at least two annular coils which are arranged in or on the elastic supporting body symmetrically to an axis of symmetry of the supporting body, one of the coils being arranged on one side of the axis of symmetry and the other one of the coils being arranged on the other side of the axis of symmetry, the annular coils being arranged in series forming a Helmholtz coil pair so that the applicator is applicable to different body parts; and
  a device for supplying a control signal to the annular coils,
 a control device which supplies signals to the applicator, and
 an external power supply unit connected to the control device, wherein the power supply unit is detachable from the control device.

2. A device for pulsed signal therapy, comprising:
 a portable applicator for pulsed signal therapy comprising:
  an elastic supporting body which can be spread over a surface and during treatment lies in a U-shape around or on a body part to be treated;
  at least two annular coils which are arranged in or on the elastic supporting body symmetrically to an axis of symmetry of the supporting body, one of the coils being arranged on one side of the axis of symmetry and the other one of the coils being arranged on the other side of the axis of symmetry, the annular coils being arranged in series forming a Helmholtz coil pair so that the applicator is applicable to different body parts; and
  a device for supplying a control signal to the annular coils,
 a control device which supplies signals to the applicator, wherein the control device is detachable from the applicator.

* * * * *